United States Patent [19]

Rieger et al.

[11] 3,944,606

[45] Mar. 16, 1976

[54] PROCESS OF PRODUCING ALKALI METAL OR AMMONIUM CITRATES

[75] Inventors: Manfred Rieger, Ludwigshafen; Johannes Kioustelidis, Mannheim, both of Germany

[73] Assignee: Joh. A. Benckiser GmbH, Ludwigshafen, Germany

[22] Filed: Oct. 29, 1974

[21] Appl. No.: 518,714

[30] Foreign Application Priority Data

Nov. 3, 1973 Germany............................ 2355059

[52] U.S. Cl................................................ 260/535 P
[51] Int. Cl.$^2$........................................ C07C 59/16
[58] Field of Search................................ 260/535 P

[56] References Cited
UNITED STATES PATENTS 3,904,684  9/1975  Tsuda et al...................... 260/535 P

FOREIGN PATENTS OR APPLICATIONS 874,030  8/1961  United Kingdom ............. 260/535 P
905,817  9/1962  United Kingdom ............. 260/535 P

*Primary Examiner*—Lorraine A. Weinberger
*Assistant Examiner*—P. J. Killos
*Attorney, Agent, or Firm*—Erich M. H. Radde

[57] ABSTRACT

Alkali metal or ammonium citrates are produced from solutions of citric acid obtained by chemical reaction or by fermentation by extraction by means of a specific water-immiscible mixture of aliphatic amines and organic solvents and re-extracting the resulting organic solvent mixture with an aqueous solution of an alkali metal hydroxide, carbonate or bicarbonate, ammonia, or their salts.

13 Claims, 2 Drawing Figures

FIG. 1  Re-extraction

PROCESS OF PRODUCING ALKALI METAL OR AMMONIUM CITRATES

BACKGROUND OF THE INVENTION

1. Field of the Invention

The present invention relates to a process of producing citrates and more particularly to the process of producing — by means of extraction — alkali metal or ammonium citrates from citric acid solutions produced by chemical methods or by fermentation.

2. Description of the Prior Art

Processes of producing alkali metal citrates from fermentation solutions have been described heretofore. It is known, for instance, to precipitate the citric acid by means of milk of lime, i.e. an aqueous suspension of calcium hydroxide, and subsequently reacting the resulting calcium citrate with an alkali metal carbonate. After removing the precipitated calcium carbonate, a trisodium citrate solution is obtained.

Alkali metal citrates have also been produced by directly neutralizing citric acid solutions. In this case, however, it is necessary to employ citric acid solutions in a substantially pure form. Both known methods are complicated and require many expensive and time consuming process steps.

It is also known to recover citric acid from its aqueous solution by means of extracting agents. Butanol-2 is used as extracting agent according to French Pat. No. 1,211,066, while German Published application No. 1,268,088 employs tri-n-butyl phosphate in mixture with hydrocarbons, ethers, esters, or ketones for this purpose. However, it was not possible to obtain satisfactory results with these known methods of extraction because the distribution coefficient in both described extraction processes is so low (about 1.0) that large amounts of the extracting agents and many extraction steps were required.

SUMMARY OF THE INVENTION

It is one object of the present invention to provide a simple, effective, and inexpensive process of extracting citric acid from its aqueous solutions obtained by chemical reaction or by fermentation, which extraction process is free of the disadvantages of the heretofore used extraction processes, and of converting the resulting extraction solutions subsequently into alkali metal citrates or ammonium citrates.

Another object of the present invention is to provide alkali metal citrates or ammonium citrates of a high degree of purity.

A further object of the present invention is to provide a mixture of extracting agents for carrying out the process of the present invention.

Other objects of the present invention and advantageous features thereof will become apparent as the description proceeds.

According to the present invention there is used a specific extracting agent which is composed of a water-immiscible mixture of an amine of the following formula

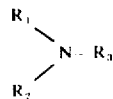

in which
R$_1$ and R$_2$ are aliphatic hydrocarbon radicals, preferably alkyl with 7 to 15 carbon atoms and
R$_3$ is hydrogen or an aliphatic hydrocarbon radical, preferably alkyl with 1 to 15 carbon atoms
and an organic solvent.

The resulting extract is subsequently treated with alkali metal hydroxide, alkali metal carbonates or bicarbonates, ammonia, or salts thereof.

Surprisingly it was found that the above mentioned mixture of amine and organic solvent used as extracting agent according to the process of the present invention has a remarkable selectivity with respect to impurities and higher distribution coefficients when extracting citric acid from its aqueous solutions than the extracting agents used according to known processes. Thus superior extraction effects are achieved.

According to the present invention the alkali metal citrates are obtained in an excellent yield and are of a high degree of purity after the organic citric acid extract is re-extracted with the alkaline solutions.

In addition thereto, the process according to the present invention has the further advantage that it is possible not only to produce trisodium citrate as it is obtained in the known reaction of calcium citrate with alkali metal carbonates, but also, depending upon the amount of the alkali metal compound used for re-extraction, to produce acid alkali metal citrate solutions. This advantage is of special importance when recovering citric acid from the alkali metal citrate solutions by means of electrodialysis. Trisodium citrate solutions are less useful for electrodialytic recovery of citric acid because their pH-value is relatively high.

Suitable amines according to the present invention are, for instance, N-lauryl-N-trialkylmethylamine such as a mixture of secondary amines whereby the sum of alkyl carbon atoms varies between 11 and 14 carbon atoms, N-methyl-di-n-octylamine, tri-isononylamine, or tri-n-decylamine. Of course, the amines must be liquid at the extraction temperature.

Suitable organic solvents according to the present invention are solvents which are not miscible with water but which have a high dissolving power for the system amine-citric acid. Hydrocarbons, alcohols, esters, ketones, or mixtures thereof can be employed as solvents. Suitable solvents, for instance, are
  a. aliphatic and alicyclic hydrocarbons such as cyclohexene, dl-limonene, or
     halogenated hydrocarbons such as carbon tetrachloride;
  b. aliphatic alcohols with 5 to 10 carbon atoms such as methyl isobutyl carbinol, 2-methyl-5-hexanol, 1-octanol, 2-ethyl-1-hexanol, or
     aromatic alcohols and phenols such as benzylalcohol, phenol, preferably as carbolxylene, i.e. an about 9% solution of phenol in xylene;
  c. aliphatic ketones such as methyl isobutyl ketone, 2-pentanone, 2-octanone, 5-methyl-3-heptanone, 2,6-dimethyl heptanone,
  d. esters, such as cyclohexylacetate or tri-n-butyl phosphate,
and others.

It is an important feature of the present invention, in order to achieve satisfactory separation of the phases and a suitable extraction equilibrium, that the proportion by volume $v$ of amine to solvent as well as the molecular proportion $m$ of amine to citric acid are properly selected. The yield of extraction is increased with an increase in the $v$-value. But this increase in the $v$-value is accompanied by the time for separation of the phases being prolonged.

The optimum proportion by volume of amine to organic solvent is within the range of about 0.05 to about 2.0 and preferably between about 0.3 to about 0.7 and the molar proportion of amine to citric acid is between about 0.5 to about 10.0 and preferably between about 1.5 and about 3.5.

When extracting citric acid from an about 8% citric acid-containing fermentation solution by means of a mixture of tri-isononylamine and methyl isobutyl ketone as solvent, the extracting solvents are preferably used in the proportion by volume of tri-isononylamine to methyl isobutyl ketone 1 : 1.5 corresponding to a $v$-value of 0.66 and in the molar proportion of amine to citric acid of 2 : 1, i.e. corresponding to an $m$-value of 2.0.

The following Table 1 shows the dependence of the distribution coefficient upon the $v$- and $m$-values. The extraction of citric acid from the fermentation solution was carried out at 20°C. Tri-isononylamine or, respectively, a mixture of tri-n-octylamine and tri-n-decylamine were used as amines and methyl isobutyl ketone or, respectively, methyl isobutyl carbinol as solvents.

organic extract is subsequently reacted with alkali metal hydroxides, ammonia, or their salts, such as the carbonates, chlorides, sulfates, or phosphates.

When using other alkali metal salts than the carbonates or bicarbonates, anionic impurities may remain in the re-extracted phase. Therefore, alkali metal sulfates or phosphates are preferably used as re-extracting agents when the resulting citrates are to be employed in detergents.

Alkali metal hydroxides, carbonates, bicarbonates, or salts are the preferred re-extracting agents although the corresponding ammonium compounds may also be used.

To achieve optimum results in said re-extraction step, selection of the equivalent proportion a of alkali metal or ammonium ions with respect to citric acid is of importance. In accordance with the present invention said equivalent proportion or ratio of equivalents of re-extracting agent with respect to citric acid in the organic extract is between about 0.1 and about 1.2 and preferably between about 0.4 and about 0.95.

By varying the a-value it is possible to produce solutions of di-alkali metal and tri-alkali metal citrates.

Acid citrate solutions can be produced from the organic extracts by extracting the citric acid not only with

TABLE 1

| Amines/Solvent | Dependence of the distribution coefficient on the v- and m-values | | | |
|---|---|---|---|---|
| | $v$ vol/vol | $m$ mol/mol | Citric acid concentration in the aqueous phase of the refined fermentation solution in weight % | Distribution coefficient |
| TINA/MIBK | 0.11 | 0.34 | 8.81 | 0.36 |
| | | 0.68 | 3.33 | 0.89 |
| TOA-TDA/MIBK | 0.25 | 0.67 | 6.36 | 1.03 |
| | | 1.34 | 1.78 | 2.77 |
| | | 2.67 | 0.58 | 5.05 |
| TINA/MIBK | 0.25 | 0.91 | 3.88 | 1.47 |
| | | 1.37 | 1.75 | 2.75 |
| | | 2.70 | 0.61 | 4.54 |
| TINA/MIBK | 0.66 | 1.33 | 3.02 | 3.33 |
| | | 1.82 | 1.68 | 4.70 |
| | | 2.65 | 0.97 | 6.02 |
| | | 5.26 | 0.42 | 7.41 |
| TOA-TDA/MIBK | 0.66 | 1.34 | 2.60 | 3.96 |
| | | 2.67 | 0.90 | 6.24 |
| | | 5.34 | 0.44 | 6.98 |
| TINA/MICA | 1.5 | 2.05 | 2.02 | 5.11 |
| | | 2.73 | 1.27 | 6.35 |
| | | 4.10 | 0.73 | 7.85 |

TINA = Tri-isononylamine
TOA-TDA = Mixture of tri-n-octylamine (TOA) and tri-n-decylamine (TDA)
MIKB = Methyl isobutyl ketone
MICA = Methyl isobutyl carbinol.

It is evident from Table 1 that the greater the $v$- and/or $m$-values, the higher is the distribution co-efficient or, respectively, the lower is the number of extraction steps required.

Extraction as well as re-extraction can be carried out discontinuously, i.e. in batch operation or, respectively, continuously, for instance, by means of a battery of mixing and separating vessels or by means of an extraction column.

In order to produce the alkali metal and/or ammonium citrates according to the present invention, the sodium carbonate and other alkali metal or ammonium carbonates or bicarbonates but also with alkali metal hydroxides or ammonia with a high distribution coefficient.

It is advisable to operate with as highly concentrated solutions of alkali metal hydroxides, ammonia, or their salts as possible. Optimum concentration values are determined by the solubility of the re-extracting agent in water as well as by the solubility of alkali metal or ammonium citrates in the resulting extract at re-extraction temperature. The preferred concentration values are also dependent on the optimum proportion by volume of the aqueous phase, i.e. the re-extracting agent to the organic phase.

On re-extracting the organic extract with alkali metal carbonates or bicarbonates, temperatures above 20° C. result in a shortening of the extraction time and in higher distribution coefficients. Therefore, re-extraction with these salts is preferably carried out at a temperature between 30° C. to 40° C.

The alkali metal or ammonium citrate solution obtained according to the present invention can be concentrated in order to produce the solid salts. Such concentration is carried out in a manner known per se. The solid salts find extensive use, for instamce, as substitutes for phosphates in detergents.

BRIEF DESCRIPTION OF THE DRAWING

The following drawings serve to illustrate the present invention and the results achieved hereby. In these drawings FIG. 1 shows, illustrated in graphs, the dependence of the distribution coefficient, free citric acid and the pH-value of the aqueous re-extraction solution from the $a$-value, while

DESCRIPTION OF THE PREFERRED EMBODIMENTS

Figure 1:
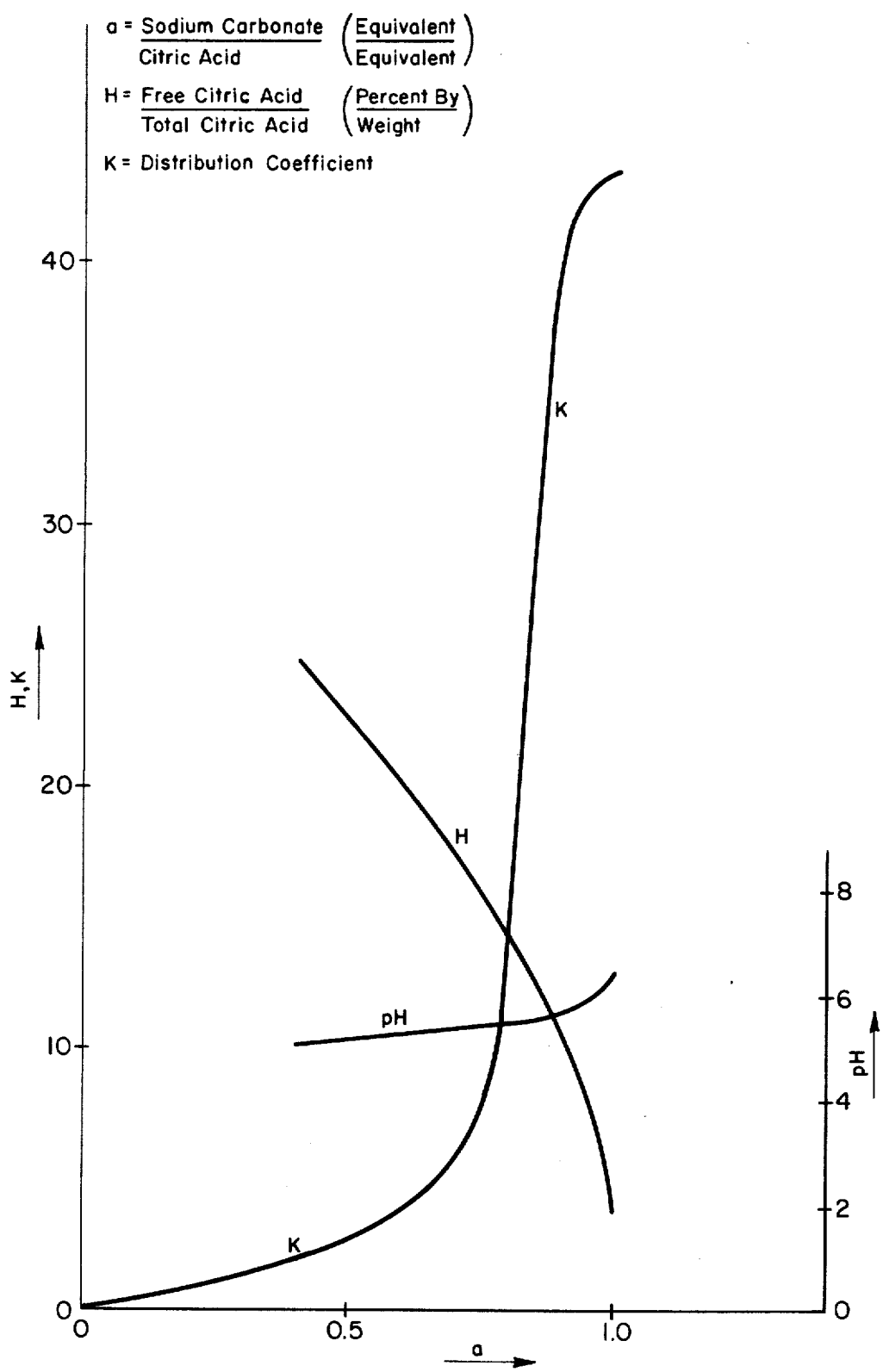

FIG. 1 graphically illustrates the interdependence of the distribution coefficient K, the free citric acid H in weight percent of total citric acid, and the pH-value of the aqueous re-extraction solution from the a value, i.e. the equivalent proportion of sodium carbonate to citric acid when using sodium carbonate solutions as re-extracting solvent.

The one ordinate shows the proportion of free citric acid to total citric acid in weight percent, designated as H and the distribution coefficient K, and the other ordinate the pH-value.

The abscissa a shows the proportion of sodium carbonate to citric acid, i.e. the equivalent proportions of these two agents.

It is evident from said FIG. 1 that by varying the $a$-value, i.e. equivalent proportion of sodium carbonate to citric acid, solutions of di- and tri-sodium citrates of varying free citric acid content can be produced.

The following examples serve to illustrate the present invention without, however, limiting the same thereto.

EXAMPLE 1

Figure 2:
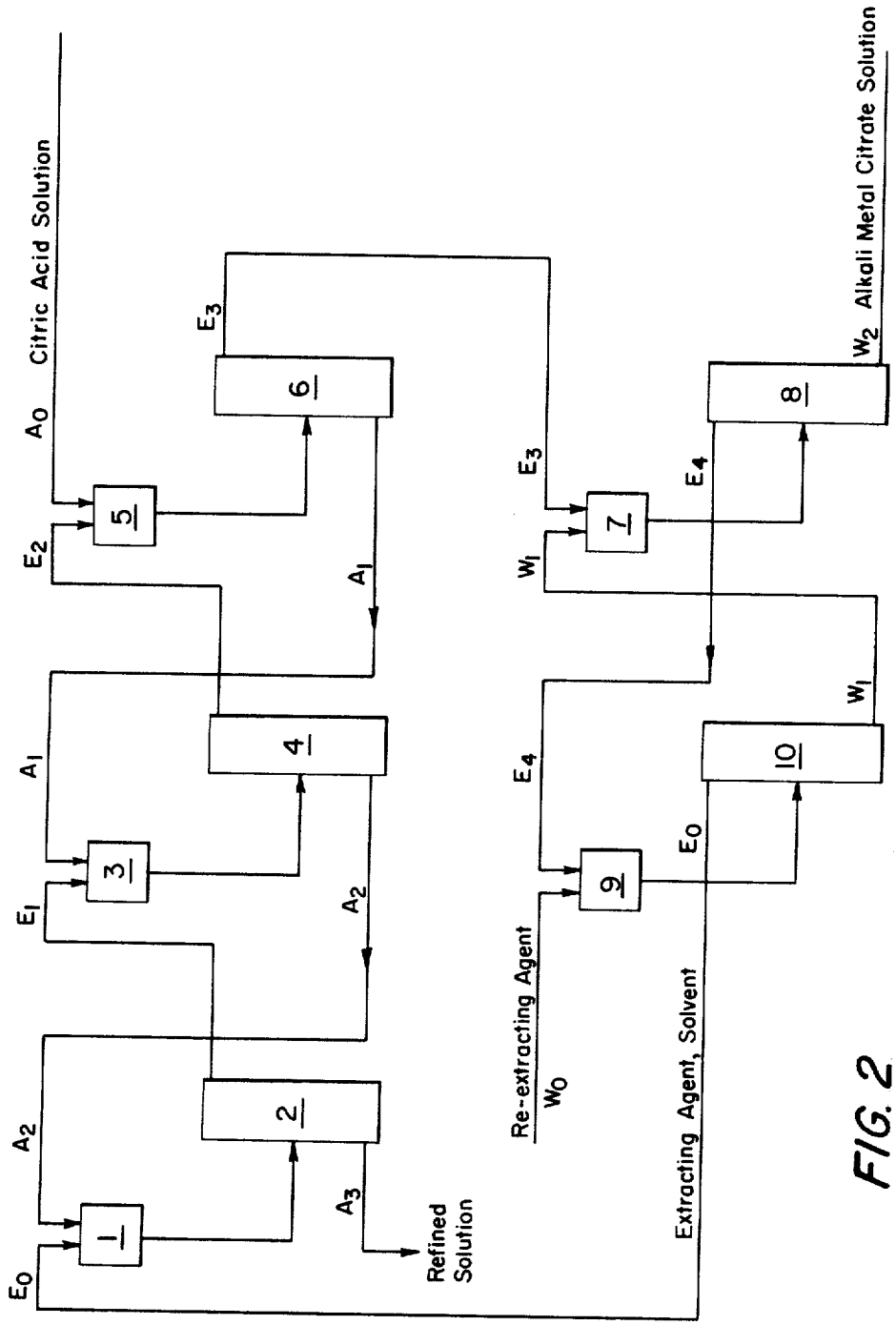
FIG. 2 illustrates diagrammatically the process according to the present invention with three extraction steps and two re-extraction steps.

A fermentation solution containing 79 g. of citric acid in each liter of solution is subjected to continuous counterflow extraction in the mixing and separating system as diagrammatically illustrated in FIG. 2, which shows a three-step extraction and a two-step re-extraction process. Of course, a larger or smaller number of extraction and/or re-extraction steps may be used depending upon the extraction conditions.

Twelve l./hr. of the organic extraction phase E0 containing 4.8 l. of tri-isononylamine and 7.2 l. of methyl isobutyl ketone and 12 l. of the aqueous phase A2 are mixed in mixing zone 1. The mixture is conducted to separator 2 from where 12 l./hr. of an about 0.3 % aqueous solution (refined solution) are discharged.

The organic phase E1 drawn off from separator 2 is mixed with 12 l./hr. of the aqueous phase A1 in mixing vessel 3 and is then introduced into separator 4. Twelve l./hr. of aqueous phase A2 and 12 l./hr. of organic phase E2 are removed.

The organic phase E2 is mixed with the fermentation solution A0 containing 79 g. of citric acid per liter solution in mixing device 5 with a speed of 12 l./hr. Thereafter, the mixture is conducted to separator 6. 12 l./hr. of the organic extract E3 containing 76.2g. of citric acid per l. of extract are drawn off from separator 6 and are mixed in mixer 7 with 6 l. of aqueous phase W1 for re-extraction. The resulting mixture is then introduced into separator 8. 6 l. of the citrate solution W2 which contains 152.4 g./l. of citric acid or, calculated as trisodium citrate dihydrate, 233.4 g./l., and 12 l. of the organic phase E4 are running off per hour. 6 l. of aqueous phase W0 which contains 114 g./l. of sodium carbonate and 12 l. of organic phase E4 are introduced into mixer 9 per hour. Mixers 7 and 9 wherein re-extraction is carried out, are kept at a temperature of 38° C. The resulting mixture is introduced into separator 10 from where 12 l./hr. of the organic phase E0 and 6 l./hr. of the aqueous phase W1 are withdrawn.

The resulting citrate solution obtained according to the present invention which is diluted to 2 percent, calculated for citric acid, has an extinction of 0.6 (determined at a wave length of 436 nm; measuring cell: 1 cm.; pH = 5.5).

In contrast thereto, an 0.2 % (calculated for citric acid) starting fermentation solution which has been adjusted to a pH of 5.5 by the addition of sodium hydroxide solution shows an extinction value of 0.5 (determined at a wave length of 436 nm; measuring cell: 1 cm.; pH = 5.5).

Thus the citrate solution obtained according to the present invention has a degree of purity of 88 percent, i.e. 88 percent of the coloring matter in the starting fermentation solution have been removed.

The purifying effect is calculated as follows:

The amount of coloring matter calculated for C g. of citric acid is $$E_o \cdot C/C_o$$

whereby $E_o$ is the extinction value of the starting solution (determined at a pH of 5.5; measuring cell: 1 cm.; wave length: 436 nm.) and $C_o$ is the amount of citric acid in 1 ml. of solution.

After carrying out extraction and re-extraction according to the present invention the amount of coloring matter in the citrate solution calculated for C g. of citric acid is $$E_e \cdot C/C_e$$

whereby $E_e$ is the extinction value of the citrate solution (determined in the same manner as the extinction value of $E_o$) and $C_e$ is the amount of citric acid in 1 ml. of citrate solution.

The purifying effect R is defined as follows:

$$R = \frac{\text{Coloring matter removed}}{\text{total sum of coloring matter}} \cdot 100 \, (\%), \text{i.e.}$$

-continued $$R = \frac{E_a \cdot C/C_a - E_e \cdot C/C_e}{E_a \cdot C/C_a} \cdot 100 \, (\%) \text{ or}$$

$$R = \left(1 - \frac{E_e \cdot C_a}{E_a \cdot C_e}\right) \cdot 100 \, (\%).$$

Thus the purifying effect in Example 1 is determined as follows:

$E_a = 0.5; E_e = 0.6;$ $C_a = 0.002 \, g.; C_e = 0.02 \, g.$ $$R = \left(1 - \frac{0.6 \cdot 0.002}{0.5 \cdot 0.02}\right) \cdot 100 \, (\%) = (1 - 0.12) \cdot 100 = 88 \, (\%).$$

EXAMPLE 2

A fermentation solution containing 71.5 g./l. of citric acid is extracted by continuous counter-current extraction in the extraction mixer/separator system described in Example 1 and FIG. 2. A mixture of tri-n-decylamine and methyl isobutyl carbinol of a volume proportion $v = 0.644$ is used as extracting agent.

The organic phases and the aqueous phases are supplied for extraction to the mixers and separators with the same speed of 12 l./hr. An about 0.3% aqueous phase (refined solution) is discharged from separator 2 while the organic extract of 68.3 g./l. of citric acid is drawn off from separator 6 and is fed into mixer 7.

On re-extraction, 12 l./hr. of the organic phase and 4 l./hr. of the aqueous phase are fed into the mixers and separators or, respectively, are withdrawn from the mixers and separators. The mixers 7 and 9 are kept in this case at room temperature.

A potassium hydroxide solution containing 162 g./l. of potassium hydroxide is used as re-extracting agent. The resulting aqueous extract which is discharged from separator 8 contains 204.9 g/l. of citric acid or, calculated as tripotassium citrate monohydrate, 346.0 g./l.

The citrate solution diluted to 2 percent (calculated as citric acid) has an extinction value of 0.72 (measured at a wave length of 436 nm.; measuring cell: 1 cm.; pH = 6.3).

The extinction of the starting fermentation solution adjusted by the addition of potassium hydroxide to a pH of 6.3 and diluted to a concentration of 0.2 percent (calculated as citric acid) in contrast thereto was 0.55 (determined under the same conditions of measurement).

Thus the purifying effect on producing said citrate solution is 87 percent.

We claim:

1. In a process of producing alkali metal or ammonium citrates from citric acid solutions produced chemically or by fermentation, by extraction, the steps which comprise a. extracting the starting citric acid solution by means of a water-immiscible solvent mixture of an amine of the formula

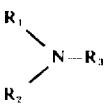

in which
 $R_1$ and $R_2$ are alkyl radicals with 7 to 15 carbon atoms and
 $R_3$ is hydrogen or an alkyl radical with 1 to 15 carbon atoms, and
 an organic solvent as extracting agent and
 b. subsequently re-extracting the resulting organic solvent extract with a compound forming alkali metal or ammonium salts of citric acid.

2. The process of claim 1, in which the proportion, by volume, of amine to organic solvent is between about 0.05 and about 2.0.

3. The process of claim 1, in which the proportion, by volume, of amine to organic solvent is between about 0.3 and 0.7.

4. The process of claim 1, in which the molar proportion of amine to citric acid is between about 0.5 and about 10.0.

5. The process of claim 1, in which the molar proportion of amine to citric acid is between about 1.5 and about 3.5.

6. The process of claim 3, in which the molar proportion of amine to citric acid is between about 0.5 and about 10.0.

7. The process of claim 3, in which the molar proportion of amine to citric acid is between about 1.5 and about 3.5.

8. The process of claim 1, in which the amine is tri-isononylamine.

9. The process of claim 1, in which the amine is tri-n-decylamine.

10. The process of claim 1, in which the organic solvent is a water-immiscible solvent selected from the group consisting of hydrocarbons, alcohols, esters, ketones, and mixtures thereof.

11. The process of claim 1, in which the equivalent proportion of re-extracting solvent to citric acid in the organic extract is between about 0.1 and about 1.2.

12. The process of claim 1, in which the equivalent proportion of re-extracting agent to citric acid in the organic extract is between about 0.4 to about 0.95.

13. The process of claim 1, in which the re-extracting agent is a solution selected from the group consisting of solutions of alkali metal hydroxides, alkali metal carbonates, alkali metal bicarbonates, ammonia, and salts of alkali metal and ammonia.

* * * * *

Disclaimer 3,944,606.—*Manfred Rieger*, Ludwigshafen, and *Johannes Kioustelidis*, Mannheim, Germany. PROCESS OF PRODUCING ALKALI METAL OR AMMONIUM CITRATES. Patent dated Mar. 16, 1976. Disclaimer filed Mar. 27, 1979, by the assignee, *Joh. A. Benckiser GmbH*.

Hereby enters this disclaimer to claims 1, 2, 3, 5, 7, 10, 11, 12 and 13 of said patent.

[*Official Gazette June 19, 1979.*]